United States Patent
Zhang (10) Patent No.: US 11,967,084 B2
(45) Date of Patent: Apr. 23, 2024

(54) PDAC IMAGE SEGMENTATION METHOD, ELECTRONIC DEVICE AND STORAGE MEDIUM

(71) Applicant: Ping An Technology (Shenzhen) Co., Ltd., Shenzhen (CN)

(72) Inventor: Ling Zhang, Bethesda, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 665 days.

(21) Appl. No.: 17/195,908

(22) Filed: Mar. 9, 2021

(65) Prior Publication Data

US 2022/0292689 A1   Sep. 15, 2022

(51) Int. Cl.
G06T 7/174 (2017.01)
A61B 5/00 (2006.01)
G06T 7/11 (2017.01)
G16H 30/40 (2018.01)

(52) U.S. Cl.
CPC .............. *G06T 7/174* (2017.01); *A61B 5/425* (2013.01); *G06T 7/11* (2017.01); *G16H 30/40* (2018.01); *G06T 2207/10081* (2013.01); *G06T 2207/10088* (2013.01); *G06T 2207/20081* (2013.01); *G06T 2207/20221* (2013.01); *G06T 2207/30096* (2013.01)

(58) Field of Classification Search
CPC . G06T 7/174; G06T 7/11; G06T 2207/10081; G06T 2207/20081; G06T 2207/20221; G06T 2207/30096; G06T 2207/20084; G16H 30/40; G16H 50/20; A61B 5/425
See application file for complete search history.

(56) References Cited

U.S. PATENT DOCUMENTS

| | | | |
|---|---|---|---|
| 10,929,981 B1* | 2/2021 | Jin | G06T 7/30 |
| 11,308,623 B2* | 4/2022 | Yuille | G06T 7/0012 |
| 2020/0063215 A1* | 2/2020 | Permuth | C12Q 1/6886 |
| 2021/0012505 A1* | 1/2021 | Yuille | G06T 7/0012 |
| 2021/0224991 A1* | 7/2021 | Yoo | A61B 8/467 |
| 2021/0295528 A1* | 9/2021 | Fuchs | G06F 18/2431 |
| 2021/0325395 A1* | 10/2021 | Borrebaeck | G01N 33/57438 |
| 2022/0072087 A1* | 3/2022 | Stein | A61K 31/4745 |
| 2022/0180506 A1* | 6/2022 | Zhao | G16H 30/40 |

(Continued)

FOREIGN PATENT DOCUMENTS

CN  111368923 A  *  7/2020  ........... G06K 9/3233

*Primary Examiner* — Wesley J Tucker
(74) *Attorney, Agent, or Firm* — ScienBiziP, P.C.

(57) ABSTRACT

A Pancreatic Ductal Adenocarcinoma (PDAC) image segmentation method, an electronic device, and a storage medium are provided. In the PDAC image segmentation method, a first model is trained using a first data set; and a second model is trained using a second data set. A third data set is obtained by annotating a to-be-annotated data set using the first model and the second model and a third model is trained using a fourth data set. A training set is obtained by modifying the first data set and the third data set using the third model and a segmentation model is obtained by training an nnUNet using the training set. A to-be-segmented PDAC image is input into the segmentation model, and a segmentation result is obtained. By utilizing the PDAC image segmentation method, a more accurate PDAC image segmentation is achieved.

20 Claims, 3 Drawing Sheets

(56) References Cited

U.S. PATENT DOCUMENTS

2022/0245810 A1\* 8/2022 Yao .................. G06V 10/82
2022/0262458 A1\* 8/2022 Senbabaoglu ......... G16B 40/30
2022/0270357 A1\* 8/2022 Goyal ................. G06T 7/11
2022/0292689 A1\* 9/2022 Zhang ................ A61B 5/425

\* cited by examiner

PDAC IMAGE SEGMENTATION METHOD, ELECTRONIC DEVICE AND STORAGE MEDIUM

FIELD

The present disclosure relates to image processing in a digital medical technology field, and particularly to a Pancreatic Ductal Adenocarcinoma (PDAC) image segmentation method, an electronic device, and a storage medium.

BACKGROUND

Comparing with human measurements, accurate and machine-automated tumor image segmentation is highly desired since it will increase the efficiency and reproducibility of complete tumor identifications, measurements, and imaging biomarkers and will enable large-scale clinical oncology patient studies that utilize medical imaging. A Pancreatic Ductal Adenocarcinoma (PDAC) image segmentation is one of the most challenging tumor segmentation tasks, yet critically important for clinical needs.

Current clinical practices carry out tumor segmentation manually, this is a wasteful consumption of labor and results in low reproducibility of derived biomarkers due to subjectivity on the part of each clinician.

DETAILED DESCRIPTION

In order to make objects, technical solutions and advantages of a present disclosure more comprehensible, the present disclosure is described in detail below with references to drawings and specific embodiments.

Figure 1:
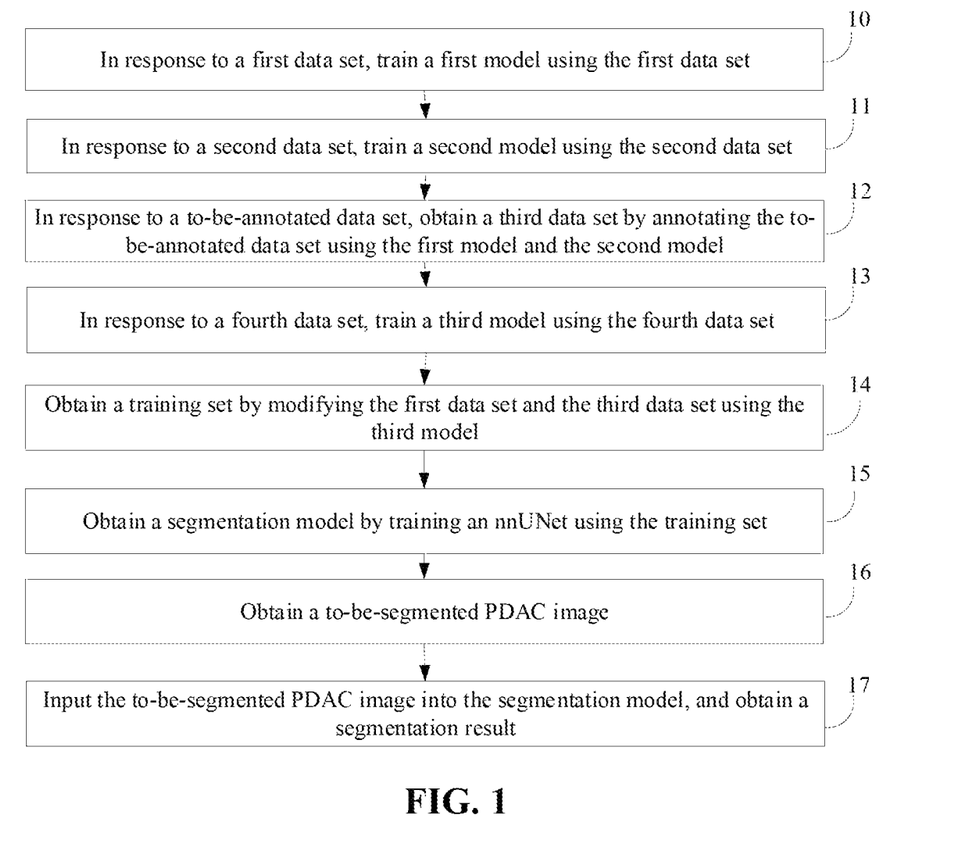
FIG. 1 is a flowchart of an embodiment of a Pancreatic Ductal Adenocarcinoma (PDAC) image segmentation method.

FIG. 1 is a flowchart of an embodiment of a Pancreatic Ductal Adenocarcinoma (PDAC) image segmentation method. According to different requirements, an order of blocks in the flowchart can be changed, and some blocks can be deleted.

The PDAC image segmentation method can be applied to one or more electronic devices. An electronic device can automatically perform numerical calculation and/or information processing according to an instruction configured or stored in advance, and hardware of the electronic device can include, but is not limited to, a microprocessor, an Application Specific Integrated Circuit (ASIC), a Field-Programmable Gate Array (FPGA), a Digital Signal Processor (DSP), and an embedded device, etc.

The electronic device can be any electronic product that can interact with users, such as a personal computer, a tablet computer, a smart phone, a personal digital assistant (PDA), a game machine, an Interactive Network Television (IPTV), and smart wearable devices, etc.

The electronic device can also be a network device and/or user equipment. The network device can include, but is not limited to, a single network server, a server group including a plurality of network servers, or a cloud computing system including a plurality of hosts or network servers.

The electronic device can be connected to a network. The network can include, but is not limited to, the Internet, a wide region network, a metropolitan region network, a local region network, a virtual private network (VPN), and the like.

At block 10, in response to a first data set, an electronic device trains a first model using the first data set.

Deep learning approaches have shown good segmentation performances for certain types of tumors, e.g., brain tumors in Magnetic Resonance Imaging (MRI), when a training dataset with multiple pixel-level fully-annotated tumor images is available. However, more often, only limited annotations can feasibly be acquired, especially for hard tumors. Previous work on the PDAC image segmentation is limited to low numbers of annotated patient images from pure venous or venous with arterial phase CT images.

For all machine learning-based tumor detection, characterization, and monitoring problems in cancer imaging, a volumetric segmentation of tumors is essential. It serves as a core for downstream processes of quantification, diagnosis, staging, prognosis, radiation planning, and treatment response prediction, all requiring a separate tumor segmentation step. Tumor-related computerized models have been evaluated using relatively small or moderate scale tumor datasets with expert annotations. Deep learning methods can increase efficiency and reproducibility and make clinical studies scalable.

It is not usually feasible to construct a large, well-organized, and volumetric-annotated tumor imaging dataset of a large number of MRI scans by experts, to train a fully-supervised deep model. The current situation is that private and/or publicly existing full annotations are moderate to small-sized, while an amount of non-annotated imaging data can be huge. Furthermore, smaller-sized tumors are more difficult to segment, especially in CT images with lower contrast than in MRI. Therefore fully automated and accurate tumor segmentation in CT/MRI is still challenging.

In one embodiment, the electronic device obtains the first data set from a preset database. For example, the preset database can be a database of any hospital.

In one embodiment, the first data set includes PDAC images of pancreas heads and uncinate regions. The first data set includes non-contrast phase Computed Tomography (CT), arterial phase CT images, and venous phase CT images with annotations of PDAC.

For example, a multi-phase pancreas and PDAC image segmentation model is trained on a private dataset A (e.g., the first data set) with registered non-contrast, arterial, and venous phases CT images. The multi-phase pancreas and PDAC image segmentation model can be denoted as the first model (hereinafter referred to as "teacher A").

In one embodiment, the electronic device may train the first model using an nnUNet backbone.

At block 11, in response to a second data set, the electronic device trains a second model using the second data set.

In one embodiment, the electronic device obtains the second data set from a public database.

In one embodiment, images in the second data set refer to a pancreatic tumor within the whole pancreas and include venous phase CT images with annotations of pancreas and tumors.

For example, a dataset B (e.g., the second data set) is a public venous phase CT dataset including manual pixel-level annotations of pancreas and tumor, and the dataset B can be used to train a segmentation model, which can be denoted as the second model (hereinafter referred to as "teacher B").

In one embodiment, the electronic device may also train the second model using an nnUNet backbone.

In one embodiment, there are no pancreas annotations in the dataset A, the electronic device uses the teacher B to create pancreas segments by division in venous phase CT images in the dataset A, thereby assisting a training of the teacher A. A combined pancreas and tumor model for PDAC tumors is obviously better than a single standalone tumor model. The teacher A and the teacher B have their specialized expertise depending on different characteristics of the dataset A and the dataset B.

At block 12, in response to a to-be-annotated data set, the electronic device obtains a third data set by annotating the to-be-annotated data set using the first model and the second model.

In one embodiment, the electronic device obtains the to-be-annotated data set from another preset database. For example, the to-be-annotated data set can be a database of another hospital.

In one embodiment, the to-be-annotated data set includes non-contrast phase CT images, arterial phase CT images, and venous phase CT images without annotations of PDAC.

In one embodiment, the electronic device annotates each image of the to-be-annotated data set using the first model and obtains a first annotation set. The electronic device annotates each image of the to-be-annotated data set using the second model and obtains a second annotation set. The electronic device fuses each image in the first annotation set and each corresponding image in the second annotation set and obtains the third data set including the fused images.

In one embodiment, for images of pancreas heads and uncinate regions, the electronic device configures a first weight for images in the first annotation set, performs a weighted fusion on the each image in the first annotation set so that the each corresponding image in the second annotation set according to the first weight, and obtains the third data set based on the weighted fusion.

In another embodiment, regarding other images except the images of the pancreas heads and the uncinate regions, the electronic device configures a second weight for images in the second annotation set, performs a weighted fusion on the each image in the first annotation set so that the each corresponding image in the second annotation set according to the second weight, and obtains the third data set.

For example, the first weight is greater than 50%, and the second weight is greater than 50%.

For example, the teacher A and the teacher B respectively apply to segment registered multi-phase CT images and venous phase CT images in a self-collected dataset C (e.g., the to-be-annotated data set). The segmentation probability maps resulting are adaptively combined and used to generate pseudo annotations of the pancreas and PDAC in the dataset C, and the third data set is obtained correspondingly.

Compared with previous self-learning methods of having one teacher model, an additional teacher model (e.g., the teacher B) is introduced to gain the benefit from knowledge in an annotated public dataset B. While a self-collected dataset A includes PDAC images of the pancreas head and the uncinate regions, the dataset B includes a variety of size distributions of pancreatic tumors spanning the whole pancreas. However, for the dataset B, pancreatic ducts, especially abnormal pancreatic ducts, can show similar appearances with PDAC images in a venous phase CT. Other types of tumors in the dataset B, such as pancreatic neuroendocrine tumors, demonstrate different image enhancement patterns with PDAC images. As a result, the teacher B tends to identify some pancreatic ducts and normal pancreas tissues as tumors. On the other hand, multi-phase (non-contrast, arterial, and venous) CT images in the dataset A can alleviate these difficulties by providing additional cues, such as dynamic enhancement patterns of different structures. By taking account of all aspects, the pseudo annotations are generated for the dataset C by a weighted combining operator on the two teachers' segmentation probability maps. At the pancreas' head and uncinate, a higher weight $\omega 0$ is assigned to the teacher A, and "$1-\omega 0$" is assigned to the teacher B. At other regions, a higher weight $\omega 1$ is assigned to the teacher B. and "$1-\omega 1$" is assigned to the teacher A. As such, the teacher A and the teacher B work together when generating pseudo annotations, which forces a student to learn from a reinforced ensemble model. Moreover, student's knowledge is expanded by learning on a large dataset C that demonstrates more PDAC variations, and it allows the student to perform better image segmentation.

At block 13, in response to a fourth data set, the electronic device trains a third model using the fourth data set.

In one embodiment, the electronic device obtains the fourth data set from another public database.

In one embodiment, the fourth data set includes images of abdominal organs and vessels and CT images with annotations of abdominal organs and vessels.

In one embodiment, the electronic device may also train the third model using an nnUNet backbone.

For example, a dataset D (e.g., the fourth data set) is a public abdominal CT dataset with annotations of major abdominal organs and vessels, and is employed for training a teaching assistant (e.g., the third model) to refine pancreas annotations in the dataset A and the dataset C. A student model is trained on both the dataset A and the dataset C with manual and/or pseudo annotations (generated as above) of the pancreas and PDAC.

At block 14, the electronic device obtains a training set by modifying the first data set and the third data set using the third model.

In one embodiment, the electronic device annotates each image in the first data set using the third model. The electronic device obtains a revised first data set by deleting non-pancreatic annotations in each image in the first data set and annotates each image in the third data set using the third model. The electronic device deletes non-pancreatic annotations in each image in the third data set and obtains a revised third data set. The electronic device obtains the training set by combining the revised first data set and the revised third data set.

For example, a semantic image parsing of organs and vessels component can act as the third model (hereinafter referred to as "teaching assistant"). The teaching assistant corrects and refines pseudo annotations of the pancreas in the dataset A and the dataset C by masking the pancreas annotations that belong to different vessel classes (e.g., portal and splenic vein, superior mesenteric vein and artery, and truncus coeliacus). As such, a final student model of a pancreas with PDAC image segmentation includes encouragement to be more focused on learning the pancreas region (with reinforced and corrected pseudo annotation) and distinguishing Pancreas and PDAC from vessels. Without the teaching assistant, some vessel regions around the pancreas can be segmented as the pancreas or PDAC even after self-learning.

At block 15, the electronic device obtains a segmentation model by training an nnUNet using the training set.

In one embodiment, the electronic device obtains a sample image set by performing down-sampling processing on each image in the training set. The electronic device performs iterative training on a three dimensional (3D) UNet stage-1 architecture by using the sample image set. The electronic device obtains a validation set and calculates a Dice value using a model generated in a current round of iteration on the verification set after each round of iteration is completed. The electronic device determines a model with a highest Dice value as the segmentation model.

For training the segmentation model, an nnUNet backbone is used due to its high accuracy on several medical image segmentation tasks, such as abdominal organs, vessels, and tumors. The 3D UNet stage-1, which trains UNet on downsampled images, is used as a network architecture, in a trade-off between training efficiency and tumor segmentation accuracy. A combination of Dice and cross-entropy loss is utilized. The model is trained to optimize loss of both pancreas and PDAC. A model that produces a best Dice score of PDAC on the validation set is selected as a preferred PDAC image segmentation model. A non-background maximal connected component is kept to remove false positives. For organ and vessel segmentation, a model is trained to optimize the overall loss of all classes.

In one embodiment, the student model is trained with the combined Data A and Data C and guided by the teaching assistant, which further corrects the pseudo pancreas annotations.

At block 16, the electronic device obtains a to-be-segmented PDAC image.

PDAC, which constitutes 90% of pancreatic cancers, has a 5-year overall survival rate of only 9%. Less than 20% of patients are eligible for an initial surgical resection. However, outcomes vary significantly even among resected patients of a same TNM (tumor, node, and metastasis) stage receiving similar treatments. Additional predictive disease biomarkers are required to permit more personalized treatment. Radiological imaging provides valuable non-invasive and information about an entire tumor. There is substantial interest in developing effective imaging-based biomarkers to stratify a group of resectable PDAC patients and predict gene mutation status from CT imaging, etc. Inserting the biomarkers into clinical practices, a robust and fully-automated PDAC image segmentation model is desirable, as the model can improve objectiveness and enable a multicentre validation on large numbers of patients. For borderline resectable and locally-advanced PDAC images, chemoradiation therapy is a suggested treatment option. One key step before each chemoradiation treatment is a manual segmentation and assessment of gross tumor volume, which is a time-consuming and complex task requiring special expertise.

At block 17, the electronic device inputs the to-be-segmented PDAC image into the segmentation model and obtains a segmentation result.

Previous PDAC image segmentation approaches are limited to small to moderate amounts of annotated images of patients (e.g., a patient number n<300) using venous or venous with arterial phase CT images. In contrast, the segmentation model is trained by using a significantly larger number of patients (e.g., n≈1000), including both self-collected and publicly available annotated and unannotated CT images covering multiple imaging phases, via a framework of self-learning. Self-learning assumes that a deep model (e.g., the segmentation model) trained from noise-filled annotations has a potential to surpass the teachers (e.g., the first model and the second model). Specifically, the segmentation model is built upon a state-of-the-art medical image segmentation backbone nnUNet, augmented using a new self-learning strategy that generates pseudo annotations on unannotated images by two teachers with different specialties, instead of traditionally by one teacher. Semantic parsing of organs and vessels around the pancreas is incorporated to further refine the pseudo annotations. The PDAC image segmentation method hereof provides an absolute improvement of 6.3% Dice score over a strong baseline of nnUNet on multi-phase CT, achieving a highest fully-automated PDAC image segmentation Dice score of 0.71 to date. A segmentation result is substantially higher than Dice scores of [0.52, 0.64] of the previous PDAC image segmentation approaches and comparable with an inter-observer variability.

According to the above embodiments, a more accurate PDAC image segmentation is achieved.

Figure 2:
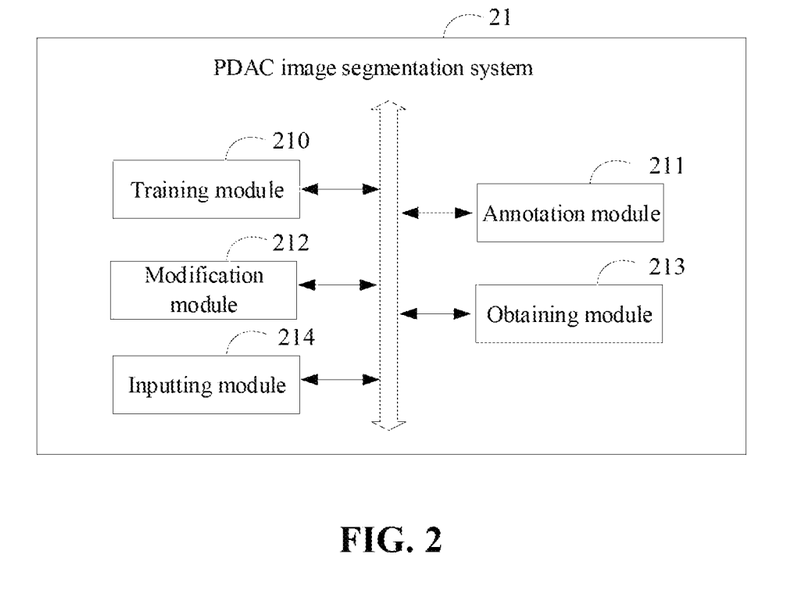
FIG. 2 is a block diagram of an embodiment of function modules of a PDAC image segmentation system.

FIG. 2 is a block diagram of an embodiment of function modules of a PDAC image segmentation system. The PDAC image segmentation system 21 includes a training module 210, an annotation module 211, a modification module 212, an obtaining module 213, and an inputting module 214. The plurality of modules includes computerized instructions in a form of one or more computer-readable programs that can be stored in a non-transitory computer-readable medium (e.g., a memory of a computer device, for example, a memory 31 in FIG. 3), and is executed by at least one processor (e.g., a processor 32 in FIG. 3) of the electronic device to implement PDAC image segmentation function (described in detail in FIG. 1).

In response to a first data set, the training module 210 trains a first model using the first data set.

Deep learning approaches have shown robust segmentation performances for certain types of tumors, e.g., brain tumors in Magnetic Resonance Imaging (MRI), when a training dataset with many pixel-level fully-annotated tumor images is available. However, more often than not, only limited annotations can feasibly be acquired, especially for hard tumors. Previous work on the PDAC image segmentation is limited to moderate amounts of annotated patient images from venous or venous with arterial phase CT images.

For all machine learning-based tumor detection, characterization, and monitoring problems in cancer imaging, a volumetric segmentation of critical tumors plays an essential role. It serves as a core for downstream processes of quantification, diagnosis, staging, prognosis, radiation planning, and treatment response prediction, all requiring a separate tumor segmentation step. Tumor-related computerized models have been evaluated using relatively small-sized or moderate scale tumor datasets with expert annotations. Deep learning methods can increase efficiency and reproducibility and make clinical studies scalable.

A large, well-organized, and volumetric-annotated tumor imaging dataset of a large number of MRI scans by experts is not usually available for training a fully-supervised deep model. A situation being faced is that private and/or publicly existing full annotations are moderate to small-sized, while an amount of unannotated imaging data can be huge. Furthermore, smaller-sized tumors are more difficult to segment, especially in CT images with lower contrast than in MRI. Therefore fully automated and accurate tumor segmentation in CT/MRI is still a challenging task to tackle.

In one embodiment, the training module 210 obtains the first data set from a preset database. For example, the preset database can be a database of any hospital.

In one embodiment, the first data set includes PDAC images of pancreas heads and uncinate regions. The first data set includes non-contrast phase Computed Tomography (CT), arterial phase CT images, venous phase CT images with annotations of PDAC.

For example, a multi-phase pancreas and PDAC image segmentation model is trained on a private dataset A (e.g., the first data set) with registered non-contrast, arterial and venous phases CT images. The multi-phase pancreas and PDAC image segmentation model are denoted as the first model (hereinafter referred to as "teacher A").

In one embodiment, the training module 210 may train the first model using an nnUNet backbone.

In response to a second data set, the training module 210 trains a second model using the second data set.

In one embodiment, the training module 210 obtains the second data set from a public database.

In one embodiment, images in the second data set refer to a pancreatic tumor of a whole pancreas and include venous phase CT images with annotations of pancreas and tumors.

For example, a dataset B (e.g., the second data set) is a public venous phase CT dataset including manual pixel-level annotations of pancreas and tumor, and the dataset B can be used to train a segmentation model, which are denoted as the second model (hereinafter referred to as "teacher B").

In one embodiment, the training module 210 may also train the second model using an nnUNet backbone.

In one embodiment, there are no pancreas annotations in the dataset A, the training module 210 uses the teacher B to divide and create pancreas segments in venous phase CT images in the dataset A, thereby assisting a training of the teacher A. A combined pancreas and tumor model segments PDAC tumors is obviously better than a single standalone tumor model. The teacher A and the teacher B have their specialized expertise depending on different characteristics of the dataset A and the dataset B.

In response to a to-be-annotated data set, the annotation module 211 obtains a third data set by annotating the to-be-annotated data set using the first model and the second model.

In one embodiment, the annotation module 211 obtains the to-be-annotated data set from another preset database. For example, the to-be-annotated data set can be a database of another hospital.

In one embodiment, the to-be-annotated data set includes ion-contrast phase CT images, arterial phase CT images, and venous phase CT images without annotations of PDAC.

In one embodiment, the annotation module 211 annotates each image of the to-be-annotated data set using the first model and obtains a first annotation set, the annotation module 211 annotates each image of the to-be-annotated data set using the second model and obtains a second annotation set. The annotation module 211 fuses each image in the first annotation set and each corresponding image in the second annotation set, and obtains the third data set including the fused images.

In one embodiment, for images of pancreas heads and uncinate regions, the annotation module 211 configures a first weight for images in the first annotation set, performs a weighted fusion on the each image in the first annotation set and the each corresponding image in the second annotation set according to the first weight, and obtains the third data set based on the weighted fusion.

In another embodiment, regarding other images except the images of the pancreas heads and the uncinate regions, the annotation module 211 configures a second weight for images in the second annotation set, performs a weighted fusion on the each image in the first annotation set and the each corresponding image in the second annotation set according to the second weight, and obtains the third data set.

For example, the first weight is greater than 50%, and the second weight is greater than 50%.

For example, the teacher A and the teacher B respectively apply to segment registered multi-phase CT images and venous phase CT images in a self-collected dataset C (e.g., the to-be-annotated data set). Resulted segmentation probability maps are adaptively combined and generated pseudo annotations of the pancreas and PDAC in the dataset C, and the third data set is obtained correspondingly.

Compared with previous self-learning methods of having one teacher model, an additional teacher model (e.g., the teacher B) is introduced to benefit from knowledge in an annotated public dataset B. While a self-collected dataset A includes PDAC images of the pancreas head and the uncinate regions, the dataset B includes a variety of size distributions of pancreatic tumors spanning the whole pancreas. However, for the dataset B, pancreatic ducts, especially abnormal pancreatic ducts, can show similar appearances with PDAC images in a venous phase CT. Other types of tumors in the dataset B, such as pancreatic neuroendocrine tumors, demonstrates different image enhancement patterns with PDAC images. As a result, the teacher B tends to identify some pancreatic ducts and normal pancreas tissues as tumors. On the other hand, multi-phase (non-contrast, arterial, and venous) CT images in the dataset A can alleviate these difficulties by providing additional cues, such as dynamic enhancement patterns of different structures. By counting in all aspects, the pseudo annotations are generated for the dataset C by a weighted combining operator on two teachers' segmentation probability maps. At the pancreas' head and uncinate, a higher weight $\omega 0$ is assigned to the teacher A, and "$1-\omega 0$" is assigned to the teacher B. At other regions, a higher weight $\omega 1$ is assigned to the teacher B, and "$1-\omega 1$" is assigned to the teacher A. As such, the teacher A and the teacher B work together when generating pseudo annotations, which forces a student to learn from a reinforced ensemble model. Moreover, student's knowledge is expanded by learning on a large dataset C that demonstrates more PDAC variations, it allows the student to perform better image segmentation.

In response to a fourth data set, the training module 210 trains a third model using the fourth data set.

In one embodiment, the training module 210 obtains the fourth data set from another public database.

In one embodiment, the fourth data set includes images of abdominal organs and vessels and CT images with annotations of abdominal organs and vessels.

In one embodiment, the training module 210 may also train the third model using an nnUNet backbone.

For example, a dataset D (e.g., the fourth data set) is a public abdominal CT dataset with annotations of major abdominal organs and vessels, and is employed here to train a teaching assistant (e.g., the third model) to refine pancreas annotations in the dataset A and the dataset C. A student model is trained on both the dataset A and the dataset C with manual and/or pseudo annotations (generated as above) of the pancreas and PDAC.

The modification module 212 obtains a training set by modifying the first data set and the third data set using the third model.

In one embodiment, the modification module 212 annotates each image in the first data set using the third model and obtains a revised first data set by deleting non-pancreatic annotations in the each image in the first data set. The modification module 212 annotates each image in the third data set using the third model. The modification module 212 deletes non-pancreatic annotations in the each image in the third data set and obtains a revised third data set. The modification module 212 obtains the training set by combining the revised first data set and the revised third data set.

For example, a semantic image parsing of organs and vessels component acts as the third model (hereinafter referred to as "teaching assistant"). The teaching assistant corrects and refines pseudo annotations of the pancreas in the dataset A and the dataset C by masking the pancreas annotations that belong to different vessel classes (e.g., portal and splenic vein, superior mesenteric vein and artery, and truncus coeliacus). As such, a final student model of pancreas with PDAC image segmentation is encouraged to be more focused on learning the pancreas region (with reinforced and corrected pseudo annotation) and distinguishing a pancreas and PDAC from vessels. Without the teaching assistant, some vessel regions around the pancreas can be segmented as the pancreas or PDAC even after self-learning.

The training module 210 obtains a segmentation model by training an nnUNet using the training set.

In one embodiment, the training module 210 obtains a sample image set by performing down-sampling processing on each image in the training set. The training module 210 performs an iterative training on a three dimensional (3D) UNet stage-1 architecture by using the sample image set. The training module 210 obtains a validation set and calculates a Dice value using a model generated in a current round of iteration on the verification set, after each round of iteration is completed. The training module 210 determines a model with a highest Dice value as the segmentation model.

For a training of the segmentation model, an nnUNet backbone is used due to its high accuracy on several medical image segmentation tasks, such as abdominal organs, vessels, and tumors. The 3D UNet stage-1, which trains UNet on downsampled images, is used as a network architecture in a trade-off between training efficiency and tumor segmentation accuracy. A combination of Dice and cross-entropy loss is utilized. The model is trained to optimize loss of both pancreas and PDAC. A model that produces a best Dice score of PDAC on the validation set is selected as a preferred PDAC image segmentation model. A non-background maximal connected component is kept to remove false positives. For organ and vessel segmentation, a model is trained to optimize the overall loss of all classes.

In one embodiment, the student model is trained with the combined Data A and Data C and guided by the teaching assistant, which further corrects the pseudo pancreas annotations.

The obtaining module 213 obtains a to-be-segmented PDAC image.

PDAC, which constitutes 90% of pancreatic cancers, has a 5-year overall survival rate only of 9%. Less than 20% of patients are eligible for an initial surgical resection. However, outcomes vary significantly even among resected patients of a same TNM (tumor, node, and metastasis) stage receiving similar treatments. There is a critical and urgent need for additional predictive disease biomarkers to permit more personalized treatment. Radiological imaging provides valuable non-invasive and informative information about an entire tumor. Subsequently, there is great interest in developing effective imaging-based biomarkers to stratify a group of resectable PDAC patients and predict gene mutation status from CT imaging, etc. Making the biomarkers available to clinical practices, a robust fully-automated PDAC image segmentation model is desirable, as the model can improve objectiveness and enable a multicentre validation on a large-scale of patient numbers. For borderline resectable and locally-advanced PDAC images, chemoradiation therapy is a suggested treatment option. One key step before each chemoradiation treatment is a manual segmentation and assessment of gross tumor volume, as a time-consuming and complex task requiring special expertise.

The inputting module 214 inputs the to-be-segmented. PDAC image into the segmentation model and obtains a segmentation result.

Previous PDAC image segmentation approaches are limited to small to moderate amounts of annotated images of patients (e.g., a patient number n<300) using venous or venous with arterial phase CT images. In contrast, the segmentation model is trained by using a significantly larger number of patients (e.g., n≈1000), including both self-collected and publicly available annotated and unannotated CT images covering multiple imaging phases, via a framework of self-learning. Self-learning assumes that a deep model (e.g., the segmentation model) trained from noise-filled annotations has a potential to surpass the teachers (e.g., the first model and the second model). Specifically, the segmentation model is built upon a state-of-the-art medical image segmentation backbone nnUNet, augmented using a new self-learning strategy that generates pseudo annotations on unannotated images by two teachers with different specialties, instead of traditionally by one teacher. Semantic parsing of organs and vessels around the pancreas is incorporated to further refine the pseudo annotations. The PDAC image segmentation method provides an absolute improvement of 6.3% Dice score over a strong baseline of nnUNet on multi-phase CT, achieving a highest fully-automated PDAC image segmentation Dice score of 0.71 to date. A segmentation result is substantially higher than Dice scores of [0.52, 0.64] of the previous PDAC image segmentation approaches and is comparable with an inter-observer variability.

According to the above embodiments, a more accurate PDAC image segmentation is achieved.

Figure 3:
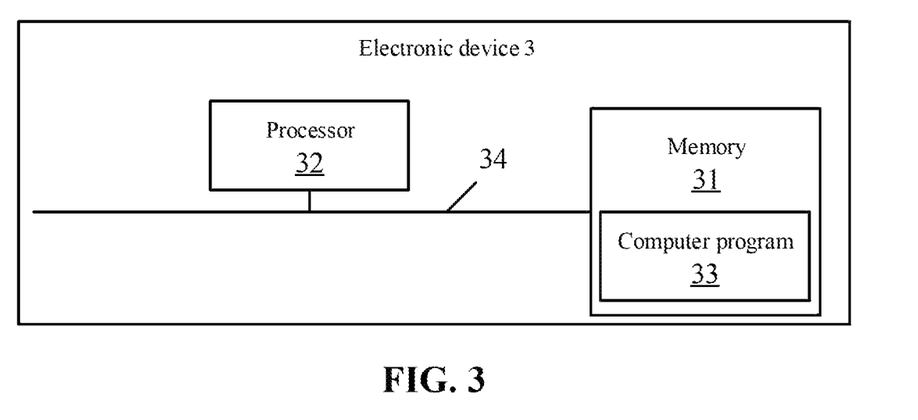
FIG. 3 is a block diagram of an embodiment of an electronic device that executes the PDAC image segmentation method.

FIG. 3 is a block diagram of an embodiment of an electronic device that executes the PDAC image segmentation method.

The electronic device 3 includes a memory 31, at least one processor 32, a computer program 33 stored in the memory 31 and operable on the at least one processor 32, and at least one communication bus 34.

It will be understood by those skilled in the art that the example shown in FIG. 3 is merely an example of the electronic device 3, it does not constitute a limitation on the electronic device 3, other examples may include more or less components than those illustrated, or may combine certain components, or have different components. The electronic device 3 may also include input and output devices, network access devices, and the like.

The at least one processor 32 may be a central processing unit (CPU) or may be another general-purpose processor, a digital signal processor (DSP), or an application specific integrated circuit (ASIC), a Field-Programmable. Gate Array (FPGA) or other programmable logic device, discrete gate or transistor logic device, discrete hardware components, and the like. The at least one processor 32 may be a microprocessor or any conventional processor or the like. The at least one processor 32 is a control center of the electronic device 3, and connects various parts of the entire electronic device 3 by using various interfaces and lines.

The memory 31 can be used to store the computer program 33 and/or modules/modules by running or executing computer programs. The data within the memory 31 implements various functions of the electronic device 3. The memory 31 may mainly include a storage program area and a storage data area, wherein the storage program area may store an operating system, an application required for at least one function (such as a sound playing function, an image playing function, etc.), and the like. Data created by use of the electronic device 3 is also stored. In addition, the memory 31 may include a non-volatile memory such as a hard disk, a memory, a plug-in hard disk, a smart memory card (SMC), and a secure digital (SD) card, flash card, at least one disk memory, flash device, or other non-volatile solid state memory.

Combined with FIG. 1, the memory 31 in the electronic device 3 stores a plurality of instructions to implement the PDAC image segmentation. When the memory 31 is executed by the at least one processor 32, the at least one processor 32 is caused to: in response to a first data set, train a first model using the first data set; in response to a second data set, train a second model using the second data set; in response to a to-be-annotated data set, obtain a third data set by annotating the to-be-annotated data set using the first model and the second model; in response to a fourth data set, train a third model using the fourth data set; obtain a training set by modifying the first data set and the third data set using the third model; obtain a segmentation model by training an nnUNet using the training set; obtain a to-be-segmented PDAC image; input the to-be-segmented PDAC image into the segmentation model, and obtain a segmentation result.

For details, refer to the description of the related steps in the corresponding embodiment of FIG. 1 for the specific implementation of the above-mentioned instructions by the at least one processor 32 is previously given.

The modules integrated in the electronic device 3, when implemented in the form of software functional modules as separate products, may be stored in a computer readable storage medium. Based on such understanding, the present disclosure implements all or part of the processes in the foregoing embodiments, and may also be completed by a computer program to instruct related hardware. The computer program may be stored in a computer readable storage medium. The methods of the various embodiments described above may be implemented when the program is executed by the processor. The computer program includes computer program codes, which may be in the form of source code, object code form, executable file, or some intermediate form. The computer readable medium may include any entity or device capable of carrying out the computer program codes, such as a recording medium, a USB flash drive, a removable hard disk, a magnetic disk, an optical disk, a computer memory, and a read-only memory (ROM).

In the several embodiments provided by the present disclosure, it should be understood that the disclosed system, apparatus, and method may be implemented in other manner. For example, the device embodiments described above are merely illustrative. For example, the division of the modules is only a logical function division, and the actual implementation may have another manner of division.

The modules described as separate components may or may not be physically separated, and the components displayed as modules may or may not be physical modules, that is, may be located in one place, or may be distributed in multiple network modules. Some or all of the modules may be selected according to actual needs to achieve the purpose of the disclosure.

In addition, each functional module in each embodiment of the present disclosure may be integrated into one processing unit, or each unit may exist as a standalone unit, or two or more modules may be integrated into one unit. The above integrated unit can be implemented in the form of hardware or in the form of hardware plus software function modules.

It should be apparent to those skilled in the art that the present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims, all changes in the meaning and scope of equivalent elements are included in the present disclosure. Any accompanying drawings in the claims should not be construed as limiting the claim. In addition, it is to be understood that the word "including" does not exclude other elements or steps. A plurality of modules or devices recited in the system claims can also be implemented by a unit or device by software or hardware. The particular ordering of words does not denote any particular order.

It should be noted that the above embodiments are only for explaining the technical solutions of the present disclosure and are not intended to be limiting, and the present disclosure describes preferred embodiments. Modifications or equivalents can be made without departing from the spirit and scope of the present disclosure.

The invention claimed is:

1. A Pancreatic Ductal Adenocarcinoma (PDAC) image segmentation method, the method comprising:
   in response to a first data set, training a first model using the first data set;
   in response to a second data set, training a second model using the second data set;
   in response to a to-be-annotated data set, obtaining a third data set by annotating the to-be-annotated data set using the first model and the second model;
   in response to a fourth data set, training a third model using the fourth data set;
   obtaining a training set by modifying the first data set and the third data set using the third model;
   obtaining a segmentation model by training an nnUNet using the training set;
   obtaining a to-be-segmented PDAC image;
   inputting the to-be-segmented PDAC image into the segmentation model, and obtaining a segmentation result.

2. The PDAC image segmentation method according to claim 1, wherein the first data set comprises PDAC images of pancreas heads and uncinate regions, the second data set comprises pancreatic tumor images of whole pancreas, and the fourth data set comprises images of abdominal organs and vessels.

3. The PDAC image segmentation method according to claim 1, wherein:
   the first data set comprises non-contrast phase Computed Tomography (CT) images, arterial phase CT images, venous phase CT images with annotations of PDAC,
   the second data set comprises venous phase CT images with annotations of pancreas and tumors, the to-be-annotated data set comprises non-contrast phase CT images, arterial phase CT images, and venous phase CT images without annotations of PDAC, and the fourth data set comprises CT images with annotations of abdominal organs and vessels.

4. The PDAC image segmentation method according to claim 1, wherein obtaining a third data set by annotating the to-be-annotated data set using the first model and the second model comprises:

annotating each image of the to-be-annotated data set using the first model and obtaining a first annotation set;

annotating each image of the to-be-annotated data set using the second model and obtaining a second annotation set;

fusing each image in the first annotation set and each corresponding image in the second annotation set and obtaining the third data set.

5. The PDAC image segmentation method according to claim 4, wherein fusing each image in the first annotation set and each corresponding image in the second annotation set and obtaining the third data set comprises:

for images of pancreas heads and uncinate regions, configuring a first weight for images in the first annotation set, performing a weighted fusion on the each image in the first annotation set and the each corresponding image in the second annotation set according to the first weight and obtaining the third data set based on the weighted fusion; or for other images except the images of the pancreas heads and the uncinate regions, configuring a second weight for images in the second annotation set, performing the weighted fusion on the each image in the first annotation set and the each corresponding image in the second annotation set according to the second weight and obtaining the third data set;

the first weight being greater than 50%, and the second weight being greater than 50%.

6. The PDAC image segmentation method according to claim 1, wherein obtaining a training set by modifying the first data set and the third data set using the third model comprises:

annotating each image in the first data set using the third model;

obtaining a revised first data set by deleting non-pancreatic annotations in the each image in the first data set;

annotating each image in the third data set using the third model;

deleting non-pancreatic annotations in the each image in the third data set and obtaining a revised third data set;

obtaining the training set by combining the revised first data set and the revised third data set.

7. The PDAC image segmentation method according to claim 1, wherein obtaining a segmentation model by training an nnUNet using the training set comprises:

obtaining a sample image set by performing down-sampling processing on each image in the training set;

performing an iterative training on a three dimensional (3D) UNet stage-1 architecture by using the sample image set;

obtaining a validation set;

calculating a Dice value using a model generated in a current round of iteration on the verification set, after each round of iteration is completed;

determining a model with a highest Dice value as the segmentation model.

8. An electronic device, comprising:
at least one processor; and
a memory storing a plurality of instructions, which when executed by the processor, causes the at least one processor to:

in response to a first data set, train a first model using the first data set;

in response to a second data set, train a second model using the second data set;

in response to a to-be-annotated data set, obtain a third data set by annotating the to-be-annotated data set using the first model and the second model;

in response to a fourth data set, train a third model using the fourth data set;

obtain a training set by modifying the first data set and the third data set using the third model;

obtain a segmentation model by training an nnUNet using the training set;

obtain a to-be-segmented PDAC image;

input the to-be-segmented PDAC image into the segmentation model, and obtain a segmentation result.

9. The electronic device according to claim 8, wherein the first data set comprises PDAC images of pancreas heads and uncinate regions, the second data set comprises pancreatic tumor images of whole pancreas, and the fourth data set comprises images of abdominal organs and vessels.

10. The electronic device according to claim 8, wherein:

the first data set comprises non-contrast phase Computed Tomography (CT) images, arterial phase CT images, venous phase CT images with annotations of PDAC, the second data set comprises venous phase CT images with annotations of pancreas and tumors, the to-be-annotated data set comprises non-contrast phase CT images, arterial phase CT images, and venous phase CT images without annotations of PDAC, and the fourth data set comprises CT images with annotations of abdominal organs and vessels.

11. The electronic device according to claim 8, wherein the at least one processor is further caused to:

annotate each image of the to-be-annotated data set using the first model and obtain a first annotation set;

annotate each image of the to-be-annotated data set using the second model and obtain a second annotation set;

fuse each image in the first annotation set and each corresponding image in the second annotation set and obtain the third data set.

12. The electronic device according to claim 11, wherein the at least one processor is further caused to:

for images of pancreas heads and uncinate regions, configure a first weight for images in the first annotation set, perform a weighted fusion on the each image in the first annotation set and the each corresponding image in the second annotation set according to the first weight and obtain the third data set based on the weighted fusion; or for other images except the images of the pancreas heads and the uncinate regions, configure a second weight for images in the second annotation set, perform the weighted fusion on the each image in the first annotation set and the each corresponding image in the second annotation set according to the second weight and obtain the third data set;

the first weight be greater than 50%, and the second weight be greater than 50%.

13. The electronic device according to claim 8, wherein the at least one processor is further caused to:

annotate each image in the first data set using the third model;

obtain a revised first data set by deleting non-pancreatic annotations in the each image in the first data set;
annotate each image in the third data set using the third model;
delete non-pancreatic annotations in the each image in the third data set and obtain a revised third data set;
obtain the training set by combining the revised first data set and the revised third data set.

14. The electronic device f according to claim 8, wherein the at least one processor is further caused to:
obtain a sample image set by performing down-sampling processing on each image in the training set;
perform an iterative training on a three dimensional (3D) UNet stage-1 architecture by using the sample image set;
obtain a validation set;
calculate a Dice value using a model generated in a current round of iteration on the verification set, after each round of iteration is completed;
determine a model with a highest Dice value as the segmentation model.

15. A non-transitory storage medium having stored thereon instructions that, when executed by a processor of an electronic device, causes the processor of the electronic device to perform a PDAC image segmentation, the method comprising:
in response to a first data set, training a first model using the first data set;
in response to a second data set, training a second model using the second data set;
in response to a to-be-annotated data set, obtaining a third data set by annotating the to-be-annotated data set using the first model and the second model;
in response to a fourth data set, training a third model using the fourth data set;
obtaining a training set by modifying the first data set and the third data set using the third model;
obtaining a segmentation model by training an nnUNet using the training set;
obtaining a to-be-segmented PDAC image;
inputting the to-be-segmented PDAC image into the segmentation model, and obtaining a segmentation result.

16. The non-transitory storage medium according to claim 15, wherein the first data set comprises PDAC images of pancreas heads and uncinate regions, the second data set comprises pancreatic tumor images of whole pancreas, and the fourth data set comprises images of abdominal organs and vessels.

17. The non-transitory storage medium according to claim 15, wherein:
the first data set comprises non-contrast phase Computed Tomography (CT) images, arterial phase CT images, venous phase CT images with annotations of PDAC,
the second data set comprises venous phase CT images with annotations of pancreas and tumors,
the to-be-annotated data set comprises non-contrast phase CT images, arterial phase CT images, and venous phase CT images without annotations of PDAC, and
the fourth data set comprises CT images with annotations of abdominal organs and vessels.

18. The non-transitory storage medium according to claim 15, wherein obtaining a third data set by annotating the to-be-annotated data set using the first model and the second model comprises:
annotating each image of the to-be-annotated data set using the first model and obtaining a first annotation set;
annotating each image of the to-be-annotated data set using the second model and obtaining a second annotation set;
fusing each image in the first annotation set and each corresponding image in the second annotation set and obtaining the third data set.

19. The non-transitory storage medium according to claim 18, wherein fusing each image in the first annotation set and each corresponding image in the second annotation set and obtaining the third data set comprises:
for images of pancreas heads and uncinate regions, configuring a first weight for images in the first annotation set, performing a weighted fusion on the each image in the first annotation set and the each corresponding image in the second annotation set according to the first weight and obtaining the third data set based on the weighted fusion; or
for other images except the images of the pancreas heads and the uncinate regions, configuring a second weight for images in the second annotation set, performing the weighted fusion on the each image in the first annotation set and the each corresponding image in the second annotation set according to the second weight and obtaining the third data set;
the first weight being greater than 50%, and the second weight being greater than 50%.

20. The non-transitory storage medium according to claim 15, wherein obtaining a training set by modifying the first data set and the third data set using the third model comprises:
annotating each image in the first data set using the third model;
obtaining a revised first data set by deleting non-pancreatic annotations in the each image in the first data set;
annotating each image in the third data set using the third model;
deleting non-pancreatic annotations in the each image in the third data set and obtaining a revised third data set;
obtaining the training set by combining the revised first data set and the revised third data set.

* * * * *